(12) United States Patent
Cohn

(10) Patent No.: US 6,516,008 B1
(45) Date of Patent: Feb. 4, 2003

(54) LASER PULSE SLICER AND DUAL WAVELENGTH CONVERTER FOR CHEMICAL SENSING

(75) Inventor: David B. Cohn, Torrance, CA (US)

(73) Assignee: Raytheon Company, Lexington, MA (US)

(*) Notice: Subject to any disclaimer, the term of this patent is extended or adjusted under 35 U.S.C. 154(b) by 75 days.

(21) Appl. No.: 09/634,216

(22) Filed: Aug. 9, 2000

(51) Int. Cl.$^7$ ................................................. H01S 3/10
(52) U.S. Cl. ............................. 372/22; 372/23; 359/28
(58) Field of Search ........................... 372/22, 32, 23; 359/28

(56) References Cited

U.S. PATENT DOCUMENTS

| | | | |
|---|---|---|---|
| 4,791,927 A | | 12/1988 | Meager |
| 5,144,630 A | * | 9/1992 | Lin ............................... 372/23 |
| 5,278,869 A | * | 1/1994 | Naya et al. ..................... 372/29 |
| 5,341,236 A | * | 8/1994 | Stappaerts ................... 359/328 |
| 5,552,926 A | * | 9/1996 | Owa et al. ................... 359/326 |
| 5,742,626 A | | 4/1998 | Mead et al. |
| 5,978,392 A | * | 11/1999 | Adachi ......................... 372/21 |
| 6,249,371 B1 | * | 6/2001 | Masuda et al. ............. 359/326 |

OTHER PUBLICATIONS

Henderson, A.J. et al., "CTUR2 Efficient Line Narrowing of an Excimer–Pumped B–Barium Borate Optical Parametric Oscillator", Proceedings of the Conference on Lasers and Electro Optics (CLEO), Anaheim, May 10–15, 1992, NY, IEEE, US, vol. Conf. 12, May 10, 1992, pp. 198–199, XP000351474, ISBN: 1–55752–237–5.

* cited by examiner

Primary Examiner—Paul Ip
Assistant Examiner—Tuan Nguyen
(74) Attorney, Agent, or Firm—Colin M. Raufer; Leonard A. Alkov; Glenn H. Lenzen, Jr.

(57) ABSTRACT

A wavelength conversion system and method. The inventive system is adapted to receive a beam of input energy having a first spiked portion with a first wavelength and a first spatial and/or temporal intensity profile and a second tail portion with the first wavelength and a second spatial and/or temporal intensity profile. The inventive system includes an electro-optic switch (14) and first polarizer (16) for directing the first portion of the input beam along a first processing path (18) and a second portion thereof along a second processing path (20). A first SHG/OPO arrangement (22, 24) is disposed in the first path (18) for shifting the wavelength of the first portion of the input energy from the first wavelength to a second wavelength. The first arrangement is optimized for the first spatial and/or temporal intensity profile of the first portion of the energy. A second SHG/OPO arrangement (30, 32) is disposed in the second path for shifting the wavelength of the second portion of the input energy from the first wavelength to the second wavelength. The second arrangement is optimized for the second spatial and/or temporal intensity profile of the second portion of the energy.

28 Claims, 2 Drawing Sheets

LASER PULSE SLICER AND DUAL WAVELENGTH CONVERTER FOR CHEMICAL SENSING

BACKGROUND OF THE INVENTION

1. Field of the Invention

The present invention relates to systems and methods for remote chemical sensing. More specifically, the present invention relates to systems and methods for laser pulse slicing and separately optimized wavelength shifting by nonlinear crystal techniques.

2. Description of the Related Art

There are numerous applications for which a system or method for remote detection of airborne chemicals is highly desirable. For military applications, by way of example, there is need for a remote chemical sensing system to detect for a deployment of chemical weapons. For commercial and industrial applications, there is a need for a remote chemical sensing system to detect pollutants, monitor processes and etc.

While many techniques have been considered for remote chemical detection, lasers have been found to be most effective. The remote detection of airborne chemicals using lasers is currently well established. The transmitter typically used for this application is a pulsed carbon dioxide ($CO_2$) laser because of its high energy capability in the 9–11 $\mu$m band where most chemicals have strong absorption features.

Unfortunately, certain chemicals and chemical weapons such as mustard gas (and others yet to be deployed) cannot be readily detected due to their very weak absorption in the band 9–11 $\mu$m band. However, mustard gas does have a strong absorption feature at 8.3 $\mu$m by which it could be easily detected. Therefore, shifting of the $CO_2$ laser wavelength to 8.3 $\mu$m band by combined second harmonic generation (SHG) and optical parametric oscillation (OPO) in nonlinear crystals is being pursued.

The typical $CO_2$ laser waveform used for this purpose is a pulse characterized by a short spike followed by a long, low intensity tail, typical of a transversely excited atmospheric (TEA) laser. The tail can contain 60% of the total pulse energy. The present approach to SHG/OPO shifting is to tailor the crystals and pump beam parameters to convert the spike without regard for the tail which, because of its much lower intensity, is not converted, wasting that portion of the total pulse energy.

Solid state lasers have been used for chemical detection; however, solid state lasers also do not generally lase in the 8.3 $\mu$m band. Efforts to shift the output wavelength of solid state lasers have met with some success. The output energies have been low and therefore the ranges have been restricted. In addition, beam quality has been poor. That is, the bandwidth of the output lines have been too broad to the extent that achieving sufficient sensing specificity has been difficult. This has limited the accuracy by which chemicals can be detected with solid state lasers.

Hence, there is a need in the art for a more effective system or method for remotely sensing new chemicals and other previously undetectable chemicals.

SUMMARY OF THE INVENTION

The need in the art is addressed by the wavelength conversion system and method of the present invention. The inventive system is adapted to receive a beam of input energy having a first portion with a first wavelength and a first spatial and/or temporal intensity profile and a second portion with the first wavelength and a second spatial and/or temporal intensity profile. The inventive system includes a mechanism for directing the first portion of the input beam along a first processing path and a second portion thereof along a second processing path. A first arrangement is disposed in the first path for shifting the wavelength of the first portion of the input energy from the first wavelength to a second wavelength. The first arrangement is optimized for the first spatial and/or temporal intensity profile of the first portion of the energy. A second arrangement is disposed in the second path for shifting the wavelength of the second portion of the input energy from the first wavelength to the second wavelength. The second arrangement is optimized for the second spatial and/or temporal intensity profile of the second portion of the energy.

In the illustrative application, the input energy is a pulse of electromagnetic energy such as might be supplied by a carbon-dioxide laser. In the illustrative embodiment, the mechanism for directing the first portion of the input beam along a first processing path and a second portion thereof along a second processing path includes an electro-optic switch adapted to rotate a polarization state of at least one of the portions of the input energy such that the first portion has a first polarization state and the second portion has a second polarization state. The output of the switch is input to a first polarizer which directs the first portion along the first path and the second portion along the second path.

In the illustrative embodiment, the first and second arrangements include a second harmonic generator that shifts the pulse first portion of the energy from the first wavelength to an intermediate wavelength. The first and second arrangements further include an optical parametric oscillator for shifting the pulse second portion of the energy from the intermediate wavelength to the second wavelength. A second polarizer is included for combining the first and second portions into a single beam.

DESCRIPTION OF THE INVENTION

Illustrative embodiments and exemplary applications will now be described with reference to the accompanying drawings to disclose the advantageous teachings of the present invention.

While the present invention is described herein with reference to illustrative embodiments for particular applications, it should be understood that the invention is not limited thereto. Those having ordinary skill in the art and access to the teachings provided herein will recognize additional modifications, applications, and embodiments within the scope thereof and additional fields in which the present invention would be of significant utility.

Figure 1:
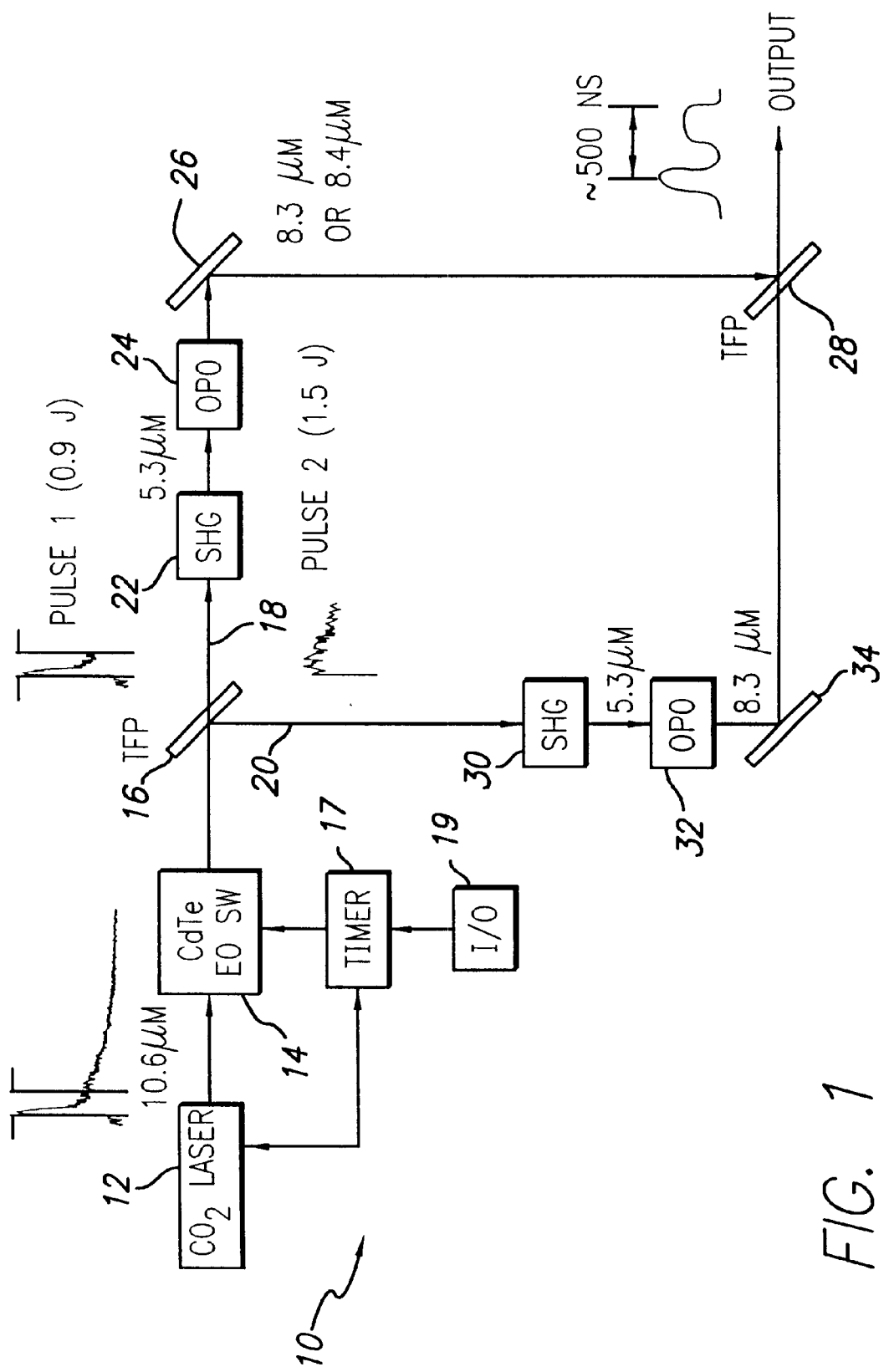
FIG. 1 is a block diagram of an illustrative embodiment of the wavelength conversion system and method of the present invention.

FIG. 1 is a block diagram of an illustrative embodiment of the wavelength conversion system and method of the present invention. The inventive system is adapted to convert energy from an input wavelength to an output wavelength. In the illustrative embodiment, the input energy is provided as a pulse at 10.6 microns ($\mu$m) by a carbon dioxide laser 12.

Figure 2:
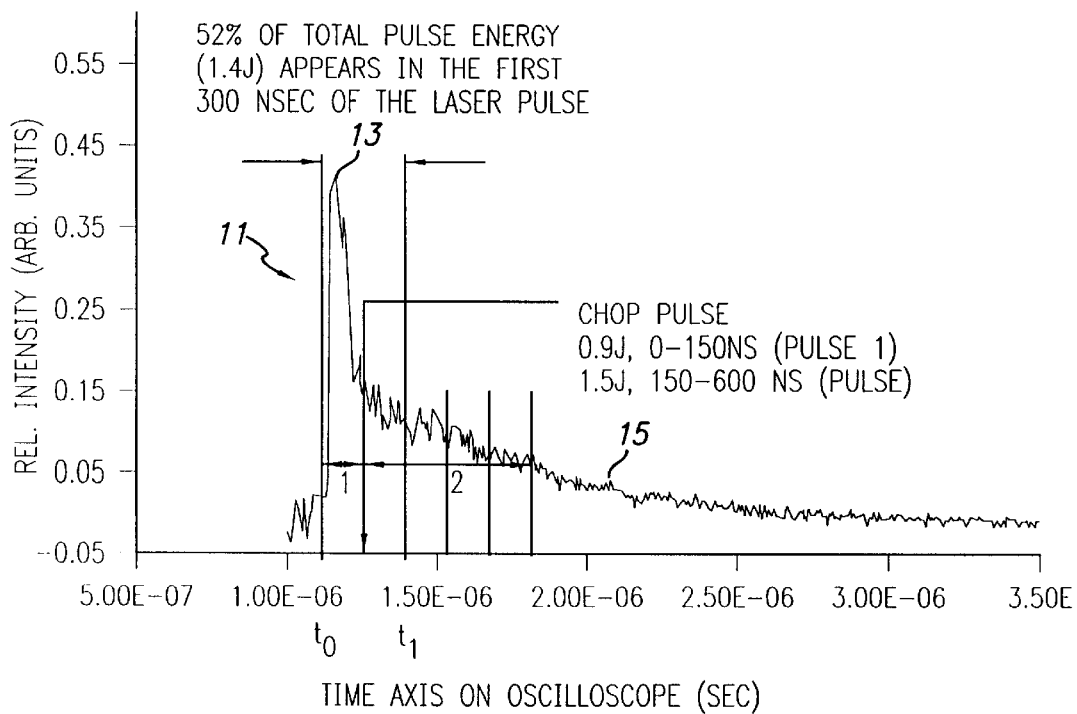
FIG. 2 is a graph of the typical temporal intensity profile of a $CO_2$ laser such as that depicted in FIG. 1.

FIG. 2 is a graph of the typical temporal intensity profile of a $CO_2$ laser such as that depicted in FIG. 1. The pulse 11 has a short spike 13 (~100 ns full width at half maximum) which begins at time to and a tail 15 which begins at time $t_1$. As shown in FIG. 2, with a typical $CO_2$ laser 12, 52% of the total pulse energy (1.4 joules) appears in the first 30.0 nanoseconds of the laser pulse between time to and $t_1$. As discussed more fully below, the inventive system 10 is effective to recover a large fraction of the pulse energy otherwise typically lost in the tail thereof using conventional methods.

Returning to FIG. 1, in accordance with the present teachings, an electro-optic switch 14 selectively switches the polarization state of the pulse of input energy 11 from a first state to a second state at time $t_1$. In the illustrative embodiment, the switch 14 is implemented with a cadmium-telluride electro-optic rotator crystal. The switch 14 operates under control of a timing circuit 17. User input may be provided via an interface 19. A thin film polarizer 16 is positioned in optical alignment with the switch 14 to split the tail from the main pulse and efficiently convert it into first and second separately tailored SHG/OPO paths 18 and 20. When the high voltage pulse 11 is applied to the switch 14, the pulse polarization is rotated and the tail 15 is shunted at 90° to the direction of the spike 13. Each path 18 and 20 is tailored to the spatial and temporal intensity profile of a respective portion of the pulse 11 input thereto.

In accordance with the present teachings, the 10.6 micron spike 13 is converted to 8.3 microns (or another wavelength) by a first second harmonic generator (SHG) 22 and a first optical parametric oscillator (OPO) 24. The SHG 22 is positioned to receive energy transmitted by the polarizer 16. In accordance with the present teachings, the first SHG 22 is designed to halve the wavelength (i.e., double the frequency) of the spike 13 from 10.6 $\mu$m to an intermediate frequency at 5.3 $\mu$m. Second harmonic generators are known in the art. In the illustrative embodiment, the SHG 22 is implemented with a silver gallium selenide crystal cut for the 10.6 micron wavelength.

The output of the SHG 22 at 5.3 $\mu$m is provided as a pump beam to the first OPO 24. Optical parametric oscillators are known in the art. In response to the pump beam, the OPO 24 outputs a signal beam at 8.3 $\mu$m and an idler beam at approximately 14.1 $\mu$m. The idler beam is dumped as is common practice.

In accordance with the present teachings, in the second path 20, the 10.6 micron tail 15 is converted to 8.3 microns (or another wavelength) by a second second harmonic generator (SHG) 30 and a second optical parametric oscillator 32. The second SHG 30 is positioned to receive the tail energy reflected by the first polarizer 16. In accordance with the present teachings, the second SHG 30 is designed to halve the wavelength (i.e., double the frequency) of the tail 15 from 10.6 $\mu$m to an intermediate frequency at 5.3 $\mu$m. As per the first SHG 22, in the illustrative embodiment, the second SHG 30 is implemented with a silver gallium selenide crystal cut for the 10.6 micron wavelength. The output of the SHG 30 at 5.3 $\mu$m is provided as a pump beam to the second OPO 32. In response to the pump beam, the second OPO 32 outputs a signal beam at 8.3 $\mu$m and an idler beam at approximately 14.1 $\mu$m. As mentioned above, the idler beam is dumped as is common practice. The signal beam at 8.3 $\mu$m output by the second OPO 32 is reflected by a fold mirror 34 to a second thin film polarizer 28. Both paths 18 and 20 are recombined at the output by the second thin film polarizer 28. That is the outputs of the first and second OPOs 24 and 32 are combined by the second thin film polarizer 28.

Not shown in FIG. 1 are resonators (mirrors) on the OPOs. As is well known in the art, the OPO resonators are partially reflecting at the signal wavelength of 8.3 $\mu$m. As will be appreciated by those skilled in the art, second harmonic generator and optical parametric oscillator crystals are cut to function (i.e. SHG or OPO), angle of incidence and antireflection specifications by vendors such as Cleveland Crystals in Cleveland, Ohio. As is well-known in the art, the angle of incidence specification is provided by the designer with respect to the crystal axis and is typically determined theoretically in a conventional manner using analysis contained in, for example, "Solid-State Laser Engineering", by W. Koechner, Springer Verlag pub, 1976.

The second path 20 can be designed to convert the pump wavelength to the same wavelength as the first path 18 for single line energy enhancement in an integrating detector. As an alternative, the second path can be tuned to another "off resonance" wavelength. The latter scheme is important, because it allows for a differential absorption measurement that can be made rapidly with a single $CO_2$ laser pulse. Inasmuch as in the illustrative embodiment, the converted "on resonance" spike and "off resonance" tail pulses are closely spaced in time (~500 ns), the measurement effectively duplicates the favorable case of a very high repetition rate laser (2 MHz) which is desirable because it effectively "freezes" the scene and eliminates atmospheric and target albedo variations. Currently, such measurements are made with a typically low repetition rate (~200 Hz) laser giving 5 ms between pulses and requiring pulse averaging to eliminate scene noise. These particular advantages described in relation to the $CO_2$ laser pertain also to any other laser type with a similar pulse profile. Including certain solid state lasers. The advantage of multi-pulse/multi-wavelength production applies to any pulsed or continuous wave laser.

In the present invention, the pulse intensity is modified by expansion/reduction optics between the intensity extremes defined by efficient conversion at the minimum and crystal optical damage at the maximum. Likewise, the tail pulse intensity is optimized through beam reduction for optimum conversion efficiency to 8.3 $\mu$m.

Figure 3:
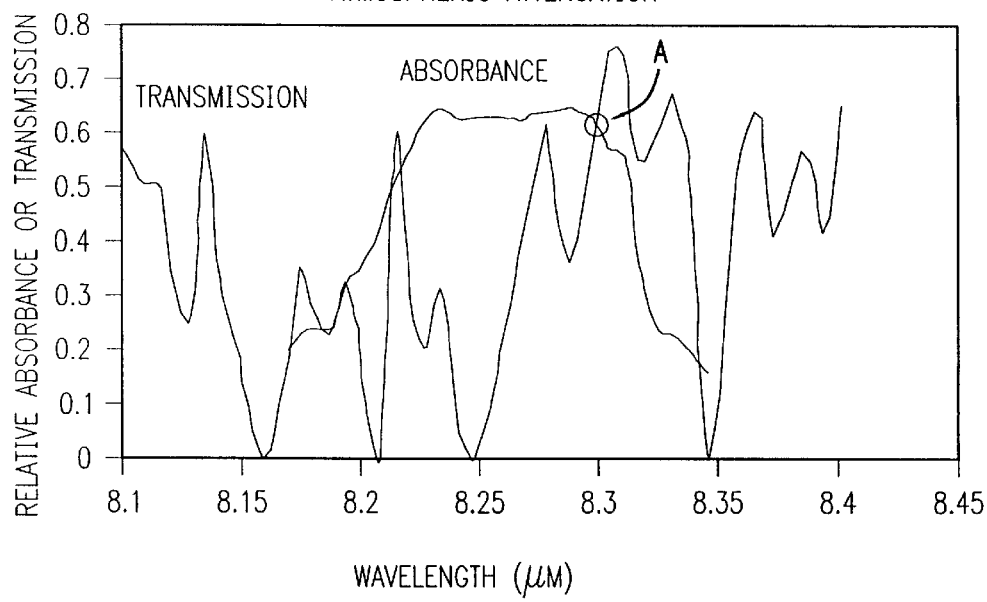
FIG. 3 is a diagram showing the absorption of mustard gas as a function of wavelength and the transmissivity of the atmosphere.

FIG. 3 is a diagram showing the absorption of mustard gas as a function of wavelength and the transmissivity of the atmosphere. As discussed above, in accordance with the present teachings, the wavelength of the output beam is chosen to provide a beam at 8.3 $\mu$m. As shown at point A in FIG. 3, at 8.3 $\mu$m, the output beam will experience good atmospheric transmissivity and it will be absorbed by the gas yielding good range and accurate detection.

For the pulse shape shown in FIG. 2, the approximate temporal separation of the two converted pulses would be about 500 ns. These pulses could be at the same wavelength or two different wavelengths, one coincident with a chemical absorption feature and one off resonance as a background interrogator. In the former case, an integrating detector with perhaps 5 MHz bandwidth could be used to integrate the pulses, giving an enhanced signal with respect to the single converted spike alone. In the latter case, a fast 2 MHz bandwidth detector could be used to resolve both pulses temporally allowing for a measurement of differential absorption and determination of the chemical concentration-path length product with a single $CO_2$ laser pump pulse.

Thus, the present invention has been described herein with reference to a particular embodiment for a particular application. Those having ordinary skill in the art and access to the present teachings will recognize additional modifications, applications and embodiments within the scope thereof. The present teachings can be used in any application for which a pulse is generated and the sections of the pulse are to be processed separately.

It is therefore intended by the appended claims to cover any and all such applications, modifications and embodiments within the scope of the present invention.

Accordingly,

What is claimed is:

1. A wavelength conversion system comprising:
    first means for receiving a pulse of input energy having a spike and a tail and directing a first portion thereof including said spike along a first processing path and a second portion thereof including said tail along a second processing path, the first portion having a first wavelength and a first spatial and/or temporal intensity profile and the second portion having the first wavelength and a second spatial and/or temporal intensity profile;
    second means disposed in the first path and optimized for the first spatial and/or temporal intensity profile of the first portion of the energy for shifting the wavelength of the first portion of the input energy from the first wavelength to a second wavelength; and
    third means disposed in the second path and optimized for the second spatial and/or temporal intensity profile of the second portion of the energy for shifting the wavelength of the second portion of the input energy from the first wavelength to the second wavelength.

2. The invention of claim 1 wherein the input energy is a pulse of laser energy.

3. The invention of claim 2 wherein the pulse of laser energy is provided by a carbon-dioxide laser.

4. The invention of claim 1 wherein the first means includes means for rotating a polarization state of at least one of the portions of the input energy whereby the first portion has a first polarization state and the second portion has a second polarization state.

5. The invention of claim 4 wherein the means for rotating a polarization state is an electro-optic switch.

6. The invention of claim 5 wherein the switch is a cadmium-telluride switch.

7. The invention of claim 4 wherein the first means further includes a first polarizer for directing the first portion along the first path and directing the second portion along the second path.

8. The invention of claim 7 further including a second polarizer for combining the first and second portions into a single beam.

9. The invention of claim 1 wherein the second means includes means for shifting the first portion of the energy from the first wavelength to an intermediate wavelength.

10. The invention of claim 9 wherein the means for shifting the first portion of the energy from the first wavelength to an intermediate wavelength includes a second harmonic generator.

11. The invention of claim 10 wherein the second harmonic generator is a crystal.

12. The invention of claim 11 wherein the crystal is silver gallium selenide.

13. The invention of claim 9 wherein the second means includes means for shifting the first portion of the energy from the intermediate wavelength to the second wavelength.

14. The invention of claim 13 wherein the means for shifting the first portion of the energy from the intermediate wavelength to the second wavelength is an optical parametric oscillator.

15. The invention of claim 14 wherein the optical parametric oscillator is a crystal.

16. The invention of claim 15 wherein the crystal is silver gallium selenide.

17. The invention of claim 1 wherein the third means includes means for shifting the second portion of the energy from the first wavelength to an intermediate wavelength.

18. The invention of claim 17 wherein the means for shifting the second portion of the energy from the first wavelength to an intermediate wavelength includes a second harmonic generator.

19. The invention of claim 18 wherein the second harmonic generator is a crystal.

20. The invention of claim 19 wherein the crystal is silver gallium selenide.

21. The invention of claim 17 wherein the third means includes means for shifting the second portion of the energy from the intermediate wavelength to the second wavelength.

22. The invention of claim 21 wherein the means for shifting the second portion of the energy from the intermediate wavelength to the second wavelength is an optical parametric oscillator.

23. The invention of claim 22 wherein the optical parametric oscillator is a crystal.

24. The invention of claim 23 wherein the crystal is silver gallium selenide.

25. A wavelength conversion system comprising:
    an electro-optic switch;
    a first polarizer in optical alignment with the switch;
    a first second harmonic generator mounted to receive a beam transmitted by the first polarizer;
    a first optical parametric oscillator in optical alignment with the first generator;
    a second second harmonic generator mounted to receive a beam reflected by the first polarizer;
    a second optical parametric oscillator in optical alignment with the second generator and
    a second polarizer in alignment with the first and the second optical parametric oscillators.

26. A wavelength conversion method including the steps of:
    receiving a pulse of input energy having a spike and a tail and directing a first portion thereof including said spike along a first processing path and a second portion thereof including said tail along a second processing path, the first portion having a first wavelength and a first spatial and/or temporal intensity profile and the second portion having the first wavelength and a second spatial and/or temporal intensity profile;
    shifting the wavelength of the first portion of the input energy from the first wavelength to a second wavelength with a first second harmonic generator and a first optical parametric oscillator disposed in the first path and optimized for the first spatial and/or temporal intensity profile of the first portion of the energy; and
    shifting the wavelength of the second portion of the input energy from the first wavelength to the second wavelength with a second harmonic generator and a second optical parametric oscillator disposed in the second path and optimized for the second spatial and/or temporal intensity profile of the second portion of the energy.

27. A system for generating a beam having a wavelength of 8.3 $\mu$m comprising:
   first means for receiving a pulse having a spike and a tail and a wavelength of 10.6 $\mu$m;
   second means for processing said spike and providing a first signal having a wavelength of 8.3 $\mu$m in response thereto;
   third means for processing said tail and providing a second signal having a wavelength of 8.3 $\mu$m in response thereto; and
   fourth means for combining said first signal and said second signal.

28. The invention of claim 27 wherein said pulse is supplied by a carbon-dioxide laser.

* * * * *

UNITED STATES PATENT AND TRADEMARK OFFICE
CERTIFICATE OF CORRECTION

PATENT NO.   : 6,516,008 B1　　　　　　　　　　　　　　　　　　　　　　　　Page 1 of 1
DATED        : February 4, 2003
INVENTOR(S)  : David B. Cohn It is certified that error appears in the above-identified patent and that said Letters Patent is hereby corrected as shown below:

<u>Column 1,</u>
Line 4, below the title, please insert -- This invention was made with Government support under Contract No. DAAD13-98-C-0021 awarded by the Department of the Army. The Government has certain rights in this invention. --.

Signed and Sealed this

Fourteenth Day of October, 2003

JAMES E. ROGAN
*Director of the United States Patent and Trademark Office*